(12) United States Patent
Koji et al.

(10) Patent No.: US 6,749,806 B2
(45) Date of Patent: Jun. 15, 2004

(54) METHOD OF STERILIZING MILDEWS AND/OR FUNGI IN THE STATE OF SPORES AND STERILIZATION APPARATUS THEREFOR

(75) Inventors: Masashi Koji, Tokyo (JP); Ken Shimizu, Tokyo (JP)

(73) Assignee: Hoshin Kagaku Sangyosho Co., Ltd., Tokyo (JP)

(*) Notice: Subject to any disclaimer, the term of this patent is extended or adjusted under 35 U.S.C. 154(b) by 0 days.

(21) Appl. No.: 10/048,357

(22) PCT Filed: May 30, 2001

(86) PCT No.: PCT/JP01/04572
§ 371 (c)(1),
(2), (4) Date: May 31, 2002

(87) PCT Pub. No.: WO01/91811
PCT Pub. Date: Dec. 6, 2001

(65) Prior Publication Data
US 2003/0082072 A1 May 1, 2003

(30) Foreign Application Priority Data
May 30, 2000 (JP) ............................... 2000-161025

(51) Int. Cl.[7] .................................................. A61L 2/00
(52) U.S. Cl. ...................... 422/24; 250/455.11; 422/22; 422/23; 422/186.3; 422/309
(58) Field of Search .......................... 422/22, 23, 24, 422/363, 309, 308; 250/455.11

(56) References Cited

U.S. PATENT DOCUMENTS

| | | | | |
|---|---|---|---|---|
| 3,617,178 A | * | 11/1971 | Clouston | 422/22 |
| 4,494,357 A | * | 1/1985 | DiGeronimo | 53/167 |
| 4,983,411 A | * | 1/1991 | Tanaka et al. | 426/234 |
| 5,547,635 A | * | 8/1996 | Duthie, Jr. | 422/24 |

FOREIGN PATENT DOCUMENTS

| | | |
|---|---|---|
| JP | 1-284255 | 11/1989 |
| JP | 2-60543 | 3/1990 |
| JP | 2-264661 | 10/1990 |
| JP | 7-116233 | 5/1995 |
| JP | 10-327747 | 12/1998 |

* cited by examiner

Primary Examiner—Krisanne M. Thornton
(74) Attorney, Agent, or Firm—Frommer Lawrence & Haug LLP; William S. Frommer; Samuel H. Megerditchian (57) ABSTRACT

The present invention relates to a method of sterilizing fungi and bacteria in a spore state for sterilizing fungi and bacteria in a spore state for sterilizing fungi and bacteria in a spore state and a sterilizer thereof. In particular, the invention is directed to a method of sterilizing sterilization targets adhering onto target-adhering things such as containers, packing materials, conveying tools, etc. or sterilization targets contained in target-containing things such as liquid, air, raw materials, etc. and also a sterilizing device thereof. Some of fungi and bacteria in a spore state are strong to ultraviolet rays, and some of them are strong to heat. So, both the fungi and so on which are strong to ultraviolet rays and those which are strong to heat can be effectively sterilized by performing successively the sterilization by UV radiation and heat.

16 Claims, 2 Drawing Sheets

METHOD OF STERILIZING MILDEWS AND/OR FUNGI IN THE STATE OF SPORES AND STERILIZATION APPARATUS THEREFOR

TECHNICAL FIELD

The present invention relates to a method of sterilizing fungi and/or bacteria in a spore state for sterilizing fungi and/or bacteria in a spore state, as sterilization targets, which are adhering to target-adhering things such as containers, packing materials, conveying tools, etc. or contained in target-containing things such as liquid, air, raw materials, etc. and a sterilizer of thereof.

BACKGROUND ART

Sterilization of fungi adhering on the surface of containers has so far been effected by irradiating ultraviolet rays over the containers when filling them up with contents such as drinks, pharmaceutical, industrial products, cosmetics before or after filling up. As a method of sterilizing fungi adhering to the containers, there are generally well known various applications such as ultraviolet rays sterilization by irradiation of ultraviolet rays, thermal sterilization by thermal application with hot water, heated steam, etc. or chemical sterilization by application of chemicals.

However, while conventional applications such as ultraviolet rays sterilization, thermal sterilization or chemical sterilization are effective only against some of the fungi, there is a problem that a satisfactory effect against other fungi cannot be expected by these applications.

Some fungi show strong tolerance against ultraviolet rays. Examples of these fungi are Chaetomium, Aspergillus and so on. Chaetomium and Aspergillus have the nature that they are strong against ultraviolet rays and also tolerant to some extent against heat, and in addition they show such powerful cellulolytic activity that ATCC 6205 strain is specified as one of the test fungi for fungicides by Japanese Industrial Standards (JIS).

Chaetomium and Aspergillus inhabit paper, pulp, vinyl, wood, etc. in addition to foods such as cereals, margarine and so on or dead leaves and soil by sticking. Their habitation distribution is global, and they are found all over Japan.

Further, there are known *Bacillus subtilis* and the like forming a spore as bacteria which are resistant to heat, though they are not classified as fungi. As a result of investigations and studies, the inventor of the present invention has found that bacteria in this spore state are very strong against heat but comparatively vulnerable to ultraviolet rays.

These Chaetomium, Aspergillus and bacteria in the spore state easily adhere to a container, a wrapping paper, a packing bag and so on because they are contained in dirty atmosphere as well as in soil, dirty water, and the like. In particular when a containers wears static electricity, its adhesive power is so strong that it is necessary to sterilize the container in order to employ the container in a hygienic state.

Therefore, the containers used for packing medical supplies, foods or the like are generally sterilized beforehand by means of ultraviolet rays or heat before filling up the containers with the contents in the filling room.

In the case where a product is to be manufactured by mass production, a method of previously producing a large number of containers and then conveying the necessary number of containers into the filling room is often adopted. A large number of containers are filled in cardboard boxes, kept in the safekeeping storage, conveyed in a encased state on a production line, picked up from the boxes onto a line conveyer and conveyed into a filling room. Therefore, when, for example, Chaetomium adheres to a cardboard container and proliferates there, the fungi may adhere to a container and are supplied on a production line.

Thus, the sterilization of a container has been performed before filling up a container by a filling device. However, Chaetomium, Aspergillus and so on are only hurt by conventional sterilization such as a method of merely irradiating ultraviolet rays or a method of merely heating, so that these fungi may not be killed completely, and sufficient sterilization of the container is not conducted.

As a result, there is a possibility that contents would be polluted through the container and the like by filling up the contents into the container with Chaetomium and the like adhering when filling up the contents into the container by a filling device. Further, there are possibilities that Chaetomium and the like move from the container into the filling room and that the filling room would be polluted with Chaetomium and the like, when the container is conveyed into the filling room.

Thus, the present invention has been established in view of these conventional problems. An object of the invention is to provide a method of sterilizing fungi and bacteria in a spore state and a sterilizer therefor which comprises enabling to sterilize fungi and bacteria in a spore state by irradiating ultraviolet rays over them to hurt them and heating the fungi and the like, or heating the fungi and the like and then irradiating ultraviolet rays over them, as a combination of UV radiation and heating, neither UV radiation only nor heating only.

DISCLOSURE OF THE INVENTION

The present invention is directed to a method of sterilizing fungi and/or bacteria in a spore state which comprises irradiating ultraviolet rays over the portions to be sterilized on target-adhering things such as containers, packing materials, conveying tools, etc. and on target-containing things such as liquid, air, raw materials, etc. to hurt sterilization targets such as fungi and/or bacteria in a spore state, which adhere to the target-adhering things or are contained in the target-containing things, and then heating the sterilization targets for sterilization.

Further, the present invention concerns a method of sterilizing fungi and/or bacteria in a spore state which comprises heating portions to be sterilized on target-adhering things such as containers, packing materials, conveying tools, etc. and on target-containing things such as liquid, air, raw materials, etc. to give thermal stimulation to the sterilization targets such as fungi and/or bacteria in a spore state, which adhere to the target-adhering things or contained in the target-containing things and then irradiating ultraviolet rays over the sterilization targets for sterilization.

In addition, the invention concerns a sterilizer of fungi and bacteria in a spore state which comprises UV radiation means for irradiating ultraviolet rays over portions to be sterilized on target-adhering things such as containers, packing materials, conveying tools, etc. or on target-containing things such as liquid and raw materials, etc. to hurt sterilization targets such as fungi and/or bacteria in a spore state, which adhere to the target-adhering things or are contained in the target-containing things, and heating means for heating the sterilization targets having wounds produced by UV radiation.

Furthermore, this invention relates to a sterilizer of fungi and bacteria in a spore state which comprises heating means for heating portions to be sterilized on target-adhering things such as containers, packing materials, conveying tools, etc. or on target-containing things such as liquid and raw materials, etc. to give thermal stimulation to sterilization targets such as fungi and/or bacteria in a spore state, which adhere to the target-adhering things or are contained in the target-containing things, and UV radiation means to irradiate ultraviolet rays over the sterilization targets having received the thermal stimulation.

BEST MODE FOR CARRYING OUT THE INVENTION

Figure 1:
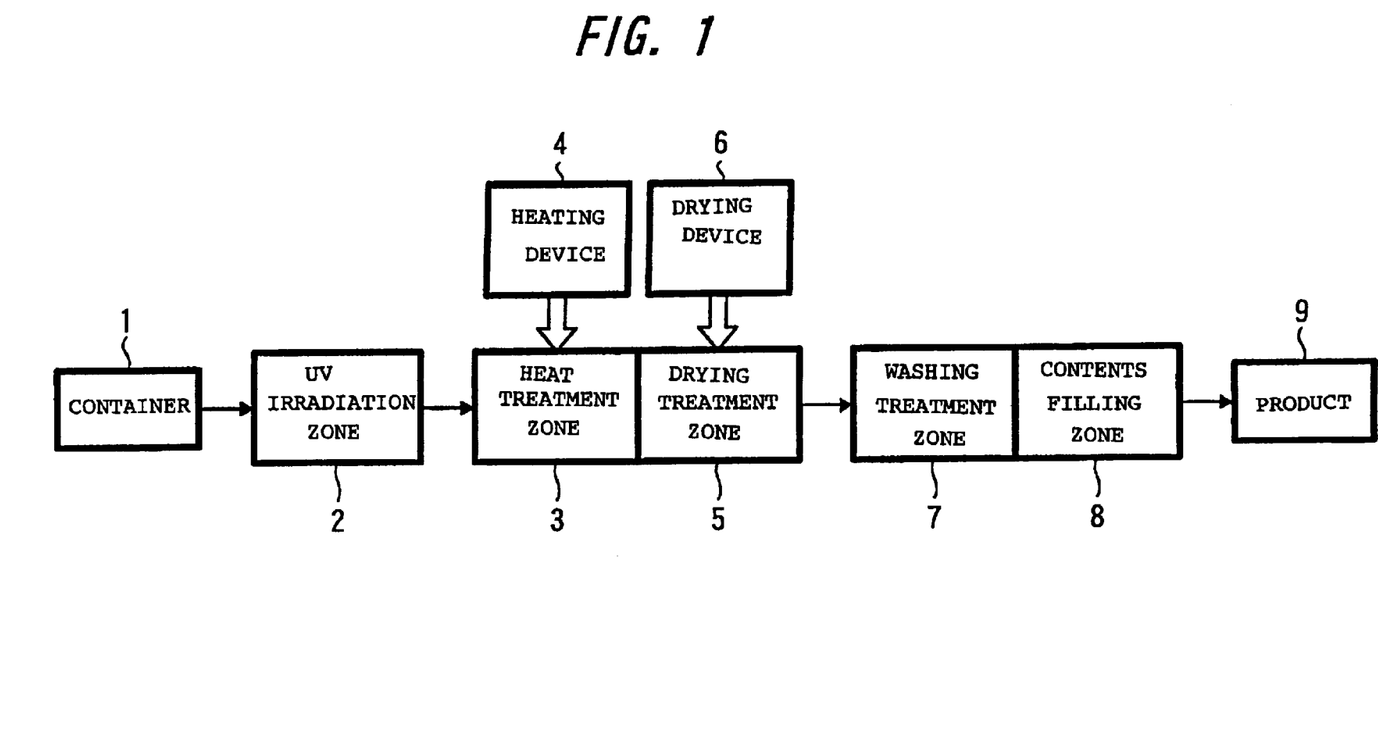
FIG. 1 is a block illustration which shows one embodiment of a method of sterilizing fungi and bacteria in a spore state of the present invention.

Preferred embodiments of the present invention will be explained below with reference to the attached drawings. FIG. 1 is a block illustration which shows the constitution of one embodiment of a method of sterilizing fungi and bacteria in a spore state of the present invention, and FIG. 2 is an illustration which shows the constitution of one embodiment of a sterilizer against fungi and bacteria in a spore state of the present invention.

Figure 2:
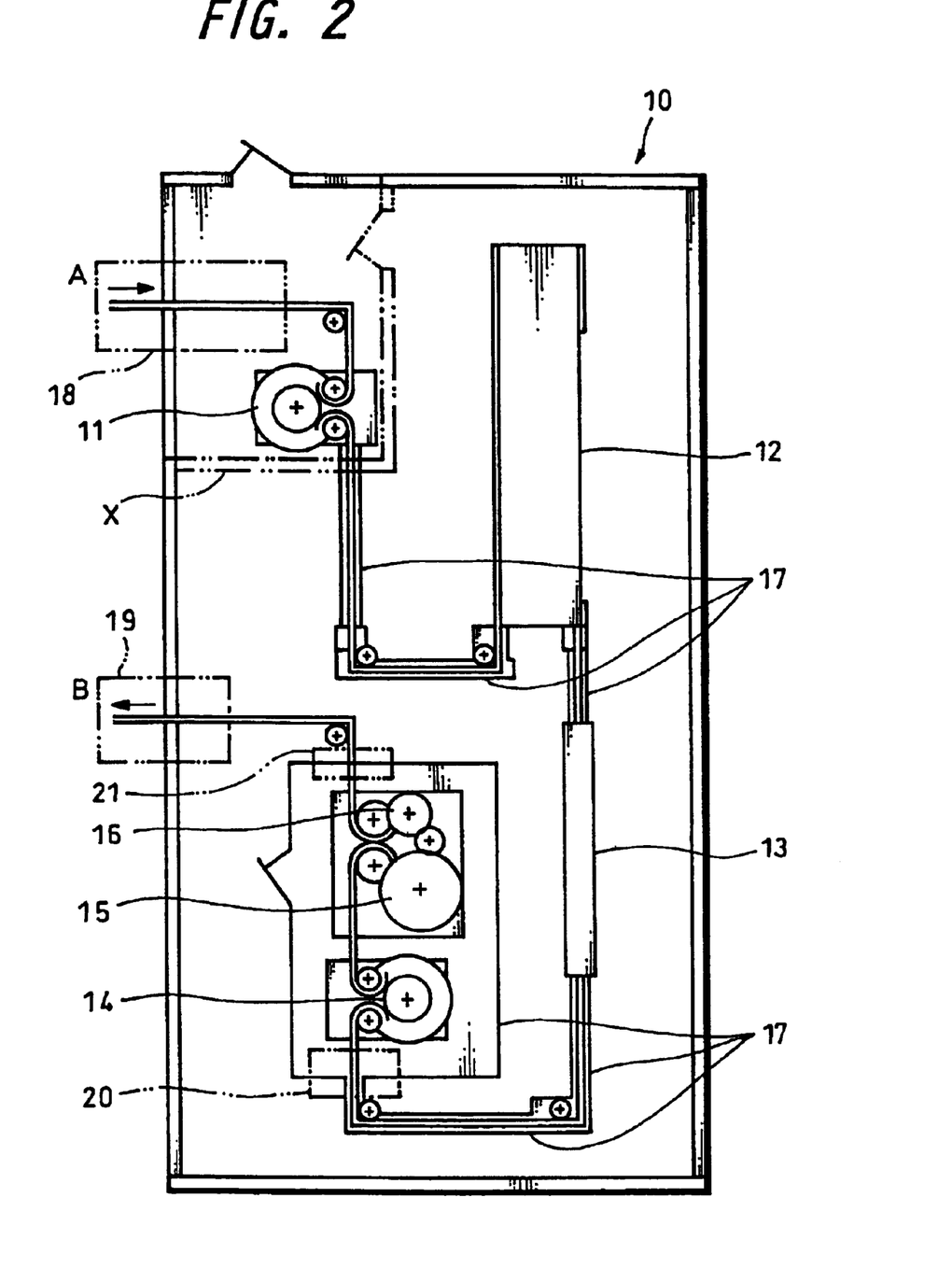
FIG. 2 is an illustration, which shows the constitution of one embodiment of the sterilizer against fungi and bacteria in a spore state of the present invention.

The method of sterilizing fungi and bacteria in a spore state and the sterilizer against them of the present invention as shown in FIG. 1 and FIG. 2 are applied to fungi and bacteria in a spore state as sterilization targets. The "fungi and so on" illustratively include *Chaetomium globosum*, *Aspergillus oryzae* and other fungi. Further, the "bacteria and so on in a spore state" illustratively include *Bacillus subtilis, Bacillus cereus*, and so on, which form spores. In addition, the sterilization targets may be, of course, directed to sterilization only for either of the fungi or bacteria in a spore state.

Target-adhering things to which sterilization targets adhere and target containing things are nominated as those that need to sterilize such sterilization targets. Here, the "target-adhering things" mean those which need sterilization because the sterilization targets will often adhere to the surface of things (inclusive of not only the surface of the front side but also the hidden parts such as the back surface of the rear side, bottom surface, dented part of the unevenness, etc.).

The target-adhering things illustratively include "container" capable of receiving drinking water, fruit drink, coffee drink, a liquid medicine, other liquid, and fixed materials such as processed food, processed vegetables and so on, "packing materials" capable of receiving one or more containers, and "conveying tool" for conveying the packing materials. Describing them more concretely, the container includes a container main body and a container lid. The container main body includes illustratively a PET bottle, a bottle, a can, a paper pack, a plastic bag, etc. and the container lid includes, for example, a plastic cap, a metal cap (aluminum, steel, etc.), a cork, etc.

For example, the packing materials include a packing box (which is made by corrugated cardboard, wood, plastic, etc.), an inside partition for packing, a wrapping paper, a bag for packing (which is made by paper, plastic, etc.), the insoles, and so on. Furthermore, the tool for conveyance includes, for example, a conveying palette made by plastic, wood, etc., a conveying board, a cabinet, a casing, and so on.

In addition, "target-containing things" mean those which need a sterilization treatment, because sterilization targets may be often impregnated or incorporated inside thereof. The target-containing things illustratively include drinking water such as city water, well water, etc., fruit drink, drink of coffee, other drinks, liquid medicines, health drink, other drugs or unregulated drugs, processed food such as boiled fish paste, sausage, etc., fixed materials such as pickle, other processed vegetables, and so on.

UV radiation means for irradiating ultraviolet rays over portions to be sterilized on target-adhering things and target-containing things include apparatuses which can emit ultraviolet rays having a wavelength of from 180 nm (nano meter) to 480 nm, for example, UV rays lamp emitting ultraviolet rays, light emitting diode (LED) capable of emitting UV rays likewise, semiconductor laser, and the like.

In addition, heating means for heating portions to be sterilized on target-adhering things and target-containing things can be classified into medium heating means capable of heating a sterilization target through a heating medium by heating a medium at a prescribed temperature and spraying the heated medium over the sterilization target and electromagnetic wave heating means capable of heating directly the sterilization target by irradiating an electromagnetic wave over the sterilization target to bring about the molecular movement in the sterilization target itself.

Of the heating means, the medium heating means illustratively include hot water heating means to use hot water as a heating medium, hot wind heating means to use hot wind as a heating medium and steam heating means to use heated steam as a heating medium. In addition, the electromagnetic wave heating means include an infrared rays irradiation device using an infrared rays lamp capable of emitting infrared rays and far infrared rays, and a laser irradiation device by using light emitting diode (LED) capable of emitting also infrared rays, etc. and a semiconductor laser capable of discharging laser light.

As shown in FIG. 1, the method of sterilizing fungi and bacteria in a spore state is composed of UV Irradiation Zone 2 to irradiate UV over the fungi and bacteria in a spore state (hereinafter referred to as "fungi and so on") adhering on Container 1 and Heat Treatment Zone 3 to heat the fungi and so on adhering on container 1 which is located in the post-stage of UV Irradiation Zone 2. Heating Device 4 is installed in Heat Treatment Zone 3 as heating means to the fungi and so on adhering on Container 1, and to the fungi and so on adhering on Container 1 are applied hot water, steam or hot wind by this Heating Device 4.

When heated water and steam are applied to the fungi and so on adhering on Container by Heating Device 4, Drying Treatment Zone 5 is provided in Heat Treatment Zone 3. In this Drying Treatment Zone 5, Drying Device 6 to supply warm wind and hot wind is provided, and drying is performed by evaporating the water of the hot water and steam remaining in Container 1, applied by Heating Device 4, by supplying Container 1 with warm wind or hot wind from this Drying Device 6.

Furthermore, Washing Treatment Zone 7 and Contents Filling Zone 8 are provided at the post-stage of Heat Treatment Zone 3. This Washing Treatment Zone 7 washes away dust, stain, foreign matter, etc. adhering onto Container 1. In Contents Filling Zone 8, contents are filled into Container 1 so that Container 1 becomes Product 9 by filling up contents into Container 1.

Fungi and so on adhering onto Container 1 can be sterilized, as shown below, according to the method of sterilizing fungi and so on adhered onto Container 1, as composed in this way. At first, Container 1 is transferred to UV Irradiation Zone 2, in which UV is irradiated. Therefore, the fungi and so on adhered onto Container 1 with weak tolerance to ultraviolet rays become extinct, but those with strong tolerance to ultraviolet rays are not killed but only hurt.

Next, Container 1 is transferred to Heat Treatment Zone 3, wherein heated water, steam or hot wind is applied over Container 1 by Heating Device 4. Container 1 turns over top and bottom, and heated water, steam or hot wind is applied over Container 1. Among the fungi and so on adhering onto Container 1, those fungi and bacteria in a spore state which have not been killed by irradiation of ultraviolet rays are killed by further application of heat over the wound due to UV radiation. Moreover, incorporation of heated water and steam into Container 1 is prevented by turning over Container 1 top and bottom. As a result, the fungi and so on adhering onto Container 1 is effectively sterilized.

When heated water and steam are applied over Container 1 by Heating Device 4 of Heat Treatment Zone 3, Container 1 is transferred to Drying Treatment Zone 5 and dried by supplying warm wind and hot wind by means of Drying Device 6. Next, Container 1 is transferred to Washing Treatment Zone 7, wherein dust, dirt, foreign matters and the like are washed away. It is filled up with contents in Contents Filling Zone 8 to give Product 9. In Heat Treatment Zone 3, this Example is characterized by applying heated water, steam or hot wind over Container 1 by Heating Device 4, but in addition, heated water, steam or hot wind may be introduced into container 1, and it may be heated.

As for a method of sterilizing fungi and so on adhering onto a container, having a constitution as described above, for example, a germ-free filling device may be used as a sterilization device, as shown in FIG. 2.

This Germ-free Filling Device 10 is composed of Preliminary Washing Device 11 to preliminarily wash the container brought in and fill up a germicidal liquid therein, at least two Coming and Going Vibration Conveyers 12 to mutually move to an opposite direction that are disposed in coupling with Preliminary Washing Device 11, Germicide-removing Outside-washing Device 13 to remove the germicidal liquid by turning the container upside down and wash the outside of the container, being coupled with this Coming and Going Vibration Conveyers 12, Germ-free-water Washing Device 14 to wash the inside of the container with germ-free water which is installed in the post-stage of Germicide-removing Outside-washing Device 13, Filling Device 15 to fill up a container which is coupled with the Germ-free-water Washing Device 14 with the contents, and Capping Device 16 to install a cap.

Further, in Germ-free Filling Device 10, a conveyer, not illustrated, is used as conveying means to each device of a container, and the conveyer and each device are covered by Tunnel 17 in which aseptic gas is supplied.

In Germ-free Filling Device 10 having such a constitution, Sterilizer 18 is disposed in an entrance A where a container is carried in. Thereby, Sterilizer 18 irradiates ultraviolet rays over a container to be carried into Germ-free Filling Device 10, and further the fungi and so on adhering onto the container is sterilized by applying heated water. The container passed through Germ-free Filling Device 10 is made free of fungi and so on. As a result, incorporation of fungi and so on into Germ-free Filling Device 10 through a container is avoided by Sterilizer 18 so that Germ-free Filling Device 10 may always hold a germfree state.

Furthermore, Germfree Filling Device 10 may be devided by a partition wall X. Then, Sterilizer 18 can achieve almost the same effect as a heating device by using heated water in Preliminary Washing Device 11.

Moreover, the sterilizer may be disposed at other positions in Germfree Filling Device 10. Thus, Sterilizer 19 of a second example is disposed in Exit B where the container of Germfree Filling Device 10 is carried out from, and the penetration of fungi and so on from the outside is prevented. Therefore, Sterilizer 19 can always keep inside of Germfree Filling Device 10 germfree.

Sterilizer 20 of a third example is provided at the pre-stage of Filling Device 15, whereby any pollution of Filling Device 15 by fungi and so on is prevented. Therefore, Filling Device 15 can prevent incorporation of fungi and so on into the contents when filling up the container with the contents.

Sterilizer 21 of a fourth example is installed in the post-stage of Filling Device 15, whereby any pollution of Filling Device 15 by fungi and so on is prevented. Therefore, Filing Device 15 can prevent incorporation of fungi and so on into the contents when filing up the container with the contents.

Experiments performed by using the devices above-described will be explained below.

Experiment 1

(1) Title of the Test

Inactivation test by ultraviolet rays sterilization lamp against *Bacillus subtilis*

(2) Object

For confirming tolerance of *Bacillus subtilis* against ultraviolet rays, this test was carried out.

(3) Test Bacteria and Quantity

*Bacillus subtilis* IF013721

Acquisition Date: Sep. 21, 1999

(4) Test Condition

Ultraviolet rays sterilization lamp: SGL-1000T5 HOSHIN (manufactured by Hoshin Sangyosho K. K.) 1

Distance from lamp pipe wall: 300 mm

UV value at stable time: 2300 $\mu$W/cm2 (Light receiving meter Topcon UVR-2)

Test container/Quantity of bacteria liquid: 90 mm watch-glass shaped plate/1 ml n=3 (Result in Table: Number of bacteria in 1 m 1)

Concentration of the test fungi: $10^3$ to $10^4$/ml UV radiation time (sec): 0, 26, 39, 78, 156

Quantity of UV radiation ($\mu$W·s/cm2): Result was shown in Table.

Adjustment of test bacteria: Dilution of acquired bacterial liquid.

Counting bacterial number: Agar dilution method

Culture condition: Normal agar nutrient medium 35±1° C. 96 hours (5) Result
Result of Inactivation test

TABLE 1

| UV Radiation Time (sec) | UV Radiation Quantity ($\mu W \cdot s/cm^2$) | Test 1 | Test 2 | Test 3 |
|---|---|---|---|---|
| 0 | 0 (No radiation) | $1.0 \times 10^4$ | $8.9 \times 10^3$ | $8.9 \times 10^3$ |
| 26 | (60000 $\mu$W/26 s) $6.0 \times 10^4$ | 1 | 0 | 0 |
| 39 | (90000 $\mu$W/39 s) $9.0 \times 10^4$ | 0 | 0 | 0 |
| 78 | (180000 $\mu$W/78 s) $1.8 \times 10^5$ | 0 | 0 | 0 |
| 156 | (360000 $\mu$W/156 s) $3.6 \times 10^5$ | 0 | 0 | 0 |

(6) Discussion

As shown in Table 1, it was considered that sterilization rate of $10^{-4}$, namely not less than 60000 $\mu$W·s/cm2 of UV illuminance was necessary under the conditions of cultivation for 96 hours.

Experiment 2

(1) Title of the Test

Inactivation test by UV radiation sterilization lamp against *Aspergillus nigar*

(2) Object

For confirming tolerance of *Aspergillus nigar* against ultraviolet rays, this test was carried out.

(3) Test Fungi and Quantity

*Aspergillus nigar* IF04414
Acquisition date: Sep. 21, 1999

(4) Test Condition

Ultraviolet rays sterilization lamp: SGL-1000T5 HOSHIN 1
Distance from the lamp pipe wall: 300 mm
UV value at stable time: 2300 $\mu$W/cm$^2$
Test container/Quantity of fungi liquid: 90 mm watch-glass shaped plate/1 ml n=3 (Result in Table: Number of fungi in 1 ml)
Concentration of the test fungi: $10^2$ to $10^3$/ml
UV radiation time (sec): 0, 7, 13, 26, 39
Quantity of UV radiation ($\mu$W·s/cm$^2$): Result was described in Table.
Adjustment of test fungi: Dilution of acquired fungi liquid.
Counting number of fungi: Agar dilution method
Culture condition: potato dextrose agar nutrient medium 27±2° C. 96 hours (5) Result Result of the inactivation test: [culture duration and degree of colony outbreak]

(6) Discussion

As shown in Table 2, there was no difference in sterilization rate with culture for 48 hours and culture for 96 hours. Sterilization rate of 99% was achieved with 90000 $\mu$W·s/cm 2. Since it is said that about 160000 $\mu$W·s/cm$^2$ is usually necessary, it is because of somewhat lower UV tolerance or less number of initial fungi as for the fungi this time.

Experiment 3

1) Title of the Test

Inactivation test by UV radiation sterilization lamp against *Chaetomium globosum* (Pretreatment with heat and hypochlorous acid)

2) Object

*Chaetomium globosum* has very strong tolerance except against heat. Thus, before testing, the following processing was performed: thermal treatment (heating at 30° C., 35° C., 40° C. each for 5 minutes), then treatment with hypochlorous acid (1 ppm, 3 ppm, 5 ppm) and furthermore UV radiation.

(3) Test Fungi and Quantity

*Chaetomium globosum* ATCC6205 1 strain (4) Test Condition

UV sterilization lamp: SGL-1000T5 HOSHIN 1
Distance from this lamp pipe wall: 300 mm
UV value at stabile time: 2300 $\mu$W/cm$^2$
Test container/quantity of fungi liquid: 90 mm watch-glass shaped plate/1 ml n=2 (Result in Table: Number of fungi in 1 ml)
Test fungi density: $10^3$ to $10^4$/ml
UV radiation time (sec)=0, 22, 44, 66
UV radiation quantity ($\mu$W·s/cm 2): Result was described in Table.
Adjustment of test fungi: Fungi were spread on potato dextrose agar plating medium one week before the test initiation. The fungi were cultured at 27±2° C., heated at 30° C., 36° C. and 40° C. each for around 5 minutes, treated with each hypochlorous acid concentration by touching for about 1 minute and subjected to UV radiation.
Counting number of fungi: Agar dilution method
Culture condition: Potato dextrose agar medium 27±2° C. 96 hours (5) Result Experiment 3-A <1> Result of inactivation test: [Culture duration and degree of colony outbreak]

<2> Thermal treatment was made at 30° C., 36° C. and 40° C. each for about 5 minutes. The fungal cells were treated with each hypochlorous acid concentration by touching for about 1 minute and subjected to UV radiation.

TABLE 2

| UV Radiation Time (sec) | UV Radiation Quantity ($\mu$W · s/cm$^2$) | Test 1 | | Test 2 | | Test 3 | |
|---|---|---|---|---|---|---|---|
| | | 48 hours | 96 hours | 48 hours | 96 hours | 48 hours | 96 hours |
| 0 | 0 | $1.4 \times 10^3$ | $1.5 \times 10^3$ | $6.0 \times 10^2$ | $6.0 \times 10^3$ | $1.1 \times 10^3$ | $1.1 \times 10^3$ |
| 7 | $1.6 \times 10^4$ | $3.8 \times 10^2$ | $3.8 \times 10^2$ | $4.1 \times 10^2$ | $4.1 \times 10^2$ | $4.0 \times 10^2$ | $4.0 \times 10^2$ |
| 13 | $3.0 \times 10^4$ | $3.0 \times 10^2$ | $3.0 \times 10^2$ | $3.1 \times 10^2$ | $3.1 \times 10^2$ | $2.8 \times 10^2$ | $2.8 \times 10^2$ |
| 26 | $6.0 \times 10^4$ | $1.3 \times 10^2$ | $1.4 \times 10^2$ | $1.2 \times 10^2$ | $1.2 \times 10^2$ | $1.2 \times 10^2$ | $1.2 \times 10^2$ |
| 39 | $9.0 \times 10^4$ | $5.8 \times 10$ | $6.2 \times 10$ | $5.1 \times 10$ | $5.5 \times 10$ | $5.7 \times 10$ | $6.7 \times 10$ |

TABLE 3

| UV Radiation Time (sec) | UV Radiation Quantity ($\mu W \cdot s/cm^2$) | hypochlorous acid concentration | 30° C. | | 36° C. | | 40° C. | |
|---|---|---|---|---|---|---|---|---|
| 0 | 0 | 1 ppm | $2.5 \times 10^3$ | $2.0 \times 10^3$ | $1.6 \times 10^3$ | $1.6 \times 10^3$ | $1.5 \times 10^3$ | $2.5 \times 10^3$ |
| | | 3 ppm | $3.2 \times 10^2$ | $3.6 \times 10^2$ | $2.6 \times 10^2$ | $2.8 \times 10^2$ | | |
| | | 5 ppm | $2.6 \times 10^2$ | $2.7 \times 10^2$ | $3.1 \times 10^2$ | $3.2 \times 10^2$ | | |
| 44 | $1.0 \times 10^5$ | 1 ppm | $1.6 \times 10^2$ | $2.0 \times 10^2$ | $1.5 \times 10^2$ | $1.7 \times 10^2$ | | |
| | | 3 ppm | $4.2 \times 10^2$ | $4.3 \times 10^2$ | $2.8 \times 10^2$ | $3.0 \times 10^2$ | | |
| | | 5 ppm | $2.9 \times 10^2$ | $3.0 \times 10^2$ | $3.4 \times 10^2$ | $3.6 \times 10^2$ | | |
| 66 | $1.5 \times 10^5$ | 1 ppm | $2.1 \times 10^2$ | $2.4 \times 10^2$ | $1.3 \times 10^2$ | $1.6 \times 10^2$ | | |
| | | 3 ppm | $2.1 \times 10^2$ | $2.2 \times 10^2$ | $3.0 \times 10^2$ | $3.1 \times 10^2$ | | |
| | | 5 ppm | $2.3 \times 10^2$ | $2.4 \times 10^2$ | $3.1 \times 10^2$ | $3.2 \times 10^2$ | | |

Explaining Experiment 3-A more in detail, it seems to have come Experiments 3-B to 3-D.

Experiment 3-B
Test Condition
Thermal treatment at 30° C. for about 5 minutes+ Treatment with hypochlorous acid Experiment 3-D
Test Condition
Thermal treatment at 40° C. for about 5 minutes+ Treatment with hypochlorous acid

TABLE 4

| UV Radiation Time (sec) | UV Radiation Quantity ($\mu W \cdot s/cm^2$) | hypochlorous acid concentration | Test 1 | | Test 2 | |
|---|---|---|---|---|---|---|
| | | | 48 hours | 96 hours | 48 hours | 96 hours |
| 0 | 0 | 1 ppm | $2.3 \times 10^3$ | $2.5 \times 10^3$ | $2.0 \times 10^3$ | $2.0 \times 10^3$ |
| | | 3 ppm | $1.8 \times 10^3$ | $1.9 \times 10^3$ | $2.0 \times 10^3$ | $2.1 \times 10^3$ |
| | | 5 ppm | $5.2 \times 10^2$ | $7.7 \times 10^2$ | $8.8 \times 10^2$ | $1.1 \times 10^3$ |
| 22 | $5.0 \times 10^4$ | 1 ppm | $2.6 \times 10^2$ | $3.8 \times 10^2$ | $1.5 \times 10^2$ | $1.9 \times 10^2$ |
| | | 3 ppm | $3.2 \times 10^2$ | $3.6 \times 10^2$ | $2.6 \times 10^2$ | $2.8 \times 10^2$ |
| | | 5 ppm | $2.6 \times 10^2$ | $2.7 \times 10^2$ | $3.1 \times 10^2$ | $3.2 \times 10^2$ |
| 44 | $1.0 \times 10^5$ | 1 ppm | $1.6 \times 10^2$ | $2.0 \times 10^2$ | $1.5 \times 10^2$ | $1.7 \times 10^2$ |
| | | 3 ppm | $4.2 \times 10^2$ | $4.3 \times 10^2$ | $2.8 \times 10^2$ | $3.0 \times 10^2$ |
| | | 5 ppm | $2.9 \times 10^2$ | $3.0 \times 10^2$ | $3.4 \times 10^2$ | $3.6 \times 10^2$ |
| 66 | $1.5 \times 10^5$ | 1 ppm | $2.1 \times 10^2$ | $2.4 \times 10^2$ | $1.3 \times 10^2$ | $1.6 \times 10^2$ |
| | | 3 ppm | $2.1 \times 10^2$ | $2.2 \times 10^2$ | $3.0 \times 10^2$ | $3.1 \times 10^2$ |
| | | 5 ppm | $2.3 \times 10^2$ | $2.4 \times 10^2$ | $3.1 \times 10^2$ | $3.2 \times 10^2$ |

Experiment 3-C
Test Condition
Thermal treatment at 36° C. for about 5 minutes+ Treatment with hypochlorous acid

TABLE 5

| UV Radiation Time (sec) | UV Radiation Quantity ($\mu W \cdot s/cm^2$) | hypochlorous acid concentration | Test 1 | | Test 2 | |
|---|---|---|---|---|---|---|
| | | | 48 hours | 96 hours | 48 hours | 96 hours |
| 0 | 0 | 1 ppm | $1.4 \times 10^3$ | $1.6 \times 10^3$ | $1.6 \times 10^3$ | $1.6 \times 10^3$ |
| | | 3 ppm | $1.8 \times 10^3$ | $1.9 \times 10^3$ | $2.0 \times 10^3$ | $2.1 \times 10^3$ |
| | | 5 ppm | $1.1 \times 10^3$ | $1.1 \times 10^3$ | $1.9 \times 10^3$ | $1.9 \times 10^3$ |
| 22 | $5.0 \times 10^4$ | 1 ppm | $2.4 \times 10^2$ | $2.9 \times 10^2$ | $2.9 \times 10^2$ | $3.3 \times 10^2$ |
| | | 3 ppm | $3.8 \times 10^2$ | $4.2 \times 10^2$ | $4.1 \times 10^2$ | $4.5 \times 10^2$ |
| | | 5 ppm | $1.9 \times 10^2$ | $2.1 \times 10^2$ | $1.9 \times 10^2$ | $2.1 \times 10^2$ |
| 44 | $1.0 \times 10^5$ | 1 ppm | $2.5 \times 10^2$ | $2.9 \times 10^2$ | $2.8 \times 10^2$ | $3.3 \times 10^2$ |
| | | 3 ppm | $2.8 \times 10^2$ | $3.1 \times 10^2$ | $2.7 \times 10^2$ | $2.9 \times 10^2$ |
| | | 5 ppm | $1.5 \times 10^2$ | $1.6 \times 10^2$ | $2.6 \times 10^2$ | $2.7 \times 10^2$ |
| 66 | $1.5 \times 10^5$ | 1 ppm | $2.6 \times 10^2$ | $2.9 \times 10^2$ | $2.4 \times 10^2$ | $2.8 \times 10^2$ |
| | | 3 ppm | $2.9 \times 10^2$ | $3.1 \times 10^2$ | $2.8 \times 10^2$ | $3.0 \times 10^2$ |
| | | 5 ppm | $2.7 \times 10^2$ | $2.8 \times 10^2$ | $1.9 \times 10^2$ | $2.0 \times 10^2$ |

TABLE 6

| UV Radiation Time (sec) | UV Radiation Quantity ($\mu W \cdot s/cm^2$) | hypochlorous acid concentration | Test 1 48 hours | Test 1 96 hours | Test 2 48 hours | Test 2 96 hours |
|---|---|---|---|---|---|---|
| 0 | 0 | 1 ppm | $1.4 \times 10^3$ | $1.5 \times 10^3$ | $2.2 \times 10^3$ | $2.5 \times 10^3$ |
|   |   | 3 ppm | $1.0 \times 10^3$ | $1.0 \times 10^3$ | $1.8 \times 10^3$ | $1.8 \times 10^3$ |
|   |   | 5 ppm | $1.9 \times 10^3$ | $1.9 \times 10^3$ | $1.4 \times 10^3$ | $1.4 \times 10^3$ |
| 22 | $5.0 \times 10^4$ | 1 ppm | $3.7 \times 10^2$ | $4.1 \times 10^2$ | $2.6 \times 10^2$ | $3.0 \times 10^2$ |
|   |   | 3 ppm | $3.1 \times 10^2$ | $3.4 \times 10^2$ | $3.0 \times 10^2$ | $3.6 \times 10^2$ |
|   |   | 5 ppm | $3.2 \times 10^2$ | $3.3 \times 10^2$ | $3.4 \times 10^2$ | $3.6 \times 10^2$ |
| 44 | $1.0 \times 10^5$ | 1 ppm | $3.7 \times 10^2$ | $4.2 \times 10^2$ | $2.9 \times 10^2$ | $3.3 \times 10^2$ |
|   |   | 3 ppm | $2.1 \times 10^2$ | $2.4 \times 10^2$ | $2.0 \times 10^2$ | $2.2 \times 10^2$ |
|   |   | 5 ppm | $2.4 \times 10^2$ | $2.5 \times 10^2$ | $2.5 \times 10^2$ | $2.7 \times 10^2$ |
| 66 | $1.5 \times 10^5$ | 1 ppm | $3.3 \times 10^2$ | $3.5 \times 10^2$ | $2.8 \times 10^2$ | $3.0 \times 10^2$ |
|   |   | 3 ppm | $2.0 \times 10^2$ | $2.2 \times 10^2$ | $2.6 \times 10^2$ | $3.0 \times 10^2$ |
|   |   | 5 ppm | $2.9 \times 10^2$ | $3.0 \times 10^2$ | $2.7 \times 10^2$ | $2.8 \times 10^2$ |

(6) Discussion

As shown in Tables 3 and 4 to 6, there was no change due to the thermal change and concentration of chemicals, but a sterilization rate of 90% was achieved by using UV radiation.

Experiment 4

1) Title of Test

Inactivation test by UV sterilization lamp against *Chaetomium globosum*

2) Object

UV tolerance of *Chaetomium globosum* was ensured, and any change on UV sterilization effect in case of fungi number: 10/100/1000 order was confirmed. Proliferation rate in culture for 48 hours and 96 hours was examined.

(3) Test Fungi and Quantity

*Chaetomium globosum* ATCC6205 1 strain (4) Test Condition

UV sterilization lamp: SGL-1000T5 HOSHIN 1
Distance from the lamp pipe wall: 300 mm
UV value at stable time: 2300 $\mu W/cm^2$ Test container/Fungi liquid quantity: 90 mm watch-glass shaped plate/1 ml n=5 (Result in Table: Number of fungi in 1 ml)

Test fungi density: 10, $10^2$, $10^3$/ml

UV radiation time (sec): 0, 22, 44, 66

UV radiation quantity ($\mu W \cdot s/cm2$): Result was described in Table.

Adjustment of Test fungi: Fungi were spread on a potato dextrose agar plating medium 1 week before the test initiation, and the fungi were cultured at 27±2° C. and provided for the test.

Counting number of fungi: Agar dilution method

Culture condition: potato dextrose agar medium, 27±2° C., 96 hours (5-1) Result 4A-1

<1> Result of the inactivation test

<2> Fungi density: 10 order/ml

TABLE 7

| UV Radiation Time (sec) | UV Radiation Quantity ($\mu W \cdot s/cm^2$) | Test 1 | Test 2 | Test 3 | Test 4 | Test 5 | Average (Sterilization rate %) |
|---|---|---|---|---|---|---|---|
| 0 | 0 | $4.0 \times 10$ | $4.1 \times 10$ | $5.5 \times 10$ | $4.8 \times 10$ | $3.4 \times 10$ | $4.4 \times 10$ |
| 22 | $5.0 \times 10^4$ | $1.1 \times 10$ | $1.7 \times 10$ | $1.7 \times 10$ | $1.2 \times 10$ | $1.4 \times 10$ | $1.4 \times 10(68.2)$ |
| 44 | $1.0 \times 10^5$ | $1.7 \times 10$ | $1.1 \times 10$ | $1.0 \times 10$ | 8 | $1.2 \times 10$ | $1.2 \times 10(72.7)$ |
| 66 | $1.5 \times 10^5$ | $1.3 \times 10$ | $1.3 \times 10$ | $1.5 \times 10$ | $1.6 \times 10$ | $1.1 \times 10$ | $1.1 \times 10(68.2)$ |

Culture duration 96 hours (5-2) Result 4A-2

<1> Result of the inactivation test [Culture duration and degree of colony outbreak]

<2> Fungi density: 10 order/ml

TABLE 8

| UV Radiation Time (sec) | UV Radiation Quantity ($\mu W \cdot s/cm^2$) | * | Test 1 | Test 2 | Test 3 | Test 4 | Test 5 |
|---|---|---|---|---|---|---|---|
| 0 | 0 | a | $3.9 \times 10$ | $4.0 \times 10$ | $5.2 \times 10$ | $4.7 \times 10$ | $3.0 \times 10$ |
|   |   | b | $4.0 \times 10$ | $4.1 \times 10$ | $5.5 \times 10$ | $4.8 \times 10$ | $3.4 \times 10$ |
| 22 | $5.0 \times 10^4$ | a | $1.1 \times 10$ | $1.7 \times 10$ | $1.7 \times 10$ | $1.2 \times 10$ | $1.2 \times 10$ |
|   |   | b | $1.1 \times 10$ | $1.7 \times 10$ | $1.7 \times 10$ | $1.2 \times 10$ | $1.4 \times 10$ |

TABLE 8-continued

| UV Radiation Time (sec) | UV Radiation Quantity ($\mu W \cdot s/cm^2$) | * | Test 1 | Test 2 | Test 3 | Test 4 | Test 5 |
|---|---|---|---|---|---|---|---|
| 44 | $1.0 \times 10^5$ | a | $1.4 \times 10$ | $1.0 \times 10$ | 9 | 8 | $1.2 \times 10$ |
|  |  | b | $1.7 \times 10$ | $1.1 \times 10$ | $10 \times 1.0$ | 8 | $1.2 \times 10$ |
| 66 | $1.5 \times 10^5$ | a | $1.0 \times 10$ | $1.3 \times 10$ | $1.5 \times 10$ | $1.6 \times 10$ | $1.0 \times 10$ |
|  |  | b | $1.3 \times 10$ | $1.3 \times 10$ | $1.5 \times 10$ | $1.6 \times 10$ | $1.1 \times 10$ |

*Culture duration a: 48 hours b: 96 hours (5-3) Result 4B-1

<1> Result of the inactivation test

<2> Fungi density: $10^2$ order/ml

TABLE 9

| UV Radiation Time (sec) | UV Radiation Quantity ($\mu W \cdot s/cm^2$) | Test 1 | Test 2 | Test 3 | Test 4 | Test 5 | Average (Sterilization rate %) |
|---|---|---|---|---|---|---|---|
| 0 | 0 | $2.8 \times 10^2$ | $3.2 \times 10^2$ | $3.3 \times 10^2$ | $3.2 \times 10^2$ | $2.9 \times 10^2$ | $3.1 \times 10^2$ |
| 22 | $5.0 \times 10^4$ | $5.1 \times 10$ | $6.7 \times 10$ | $7.6 \times 10$ | $1.1 \times 10^2$ | $8.9 \times 10$ | $7.9 \times 10$ (84.2) |
| 44 | $1.0 \times 10^5$ | $4.3 \times 10$ | $5.8 \times 10$ | $5.6 \times 10$ | $8.5 \times 10$ | $7.8 \times 10$ | $6.4 \times 10$ (79.4) |
| 66 | $1.5 \times 10^5$ | $2.7 \times 10$ | $6.5 \times 10$ | $5.3 \times 10$ | $3.7 \times 10$ | $4.9 \times 10$ | $4.9 \times 10$ (84.2) |

(5-4) Result 4B-2

<1> Result of the Inactivation test [culture duration and degree of colony outbreak]

<2> Fungi density: $10^2$ order/ml (test)

TABLE 10

| UV Radiation Time (sec) | UV Radiation Quantity ($\mu W \cdot s/cm^2$) | * | Test 1 | Test 2 | Test 3 | Test 4 | Test 5 |
|---|---|---|---|---|---|---|---|
| 0 | 0 | a | $2.8 \times 10^2$ | $3.2 \times 10^2$ | $3.3 \times 10^2$ | $3.2 \times 10^2$ | $2.8 \times 10^2$ |
|  |  | b | $2.8 \times 10^2$ | $3.2 \times 10^2$ | $3.3 \times 10^2$ | $3.2 \times 10^2$ | $2.9 \times 10^2$ |
| 22 | $5.0 \times 10^4$ | a | $4.9 \times 10$ | $6.7 \times 10$ | $7.3 \times 10$ | $1.1 \times 10^2$ | $8.8 \times 10$ |
|  |  | b | $5.1 \times 10$ | $6.7 \times 10$ | $7.6 \times 10$ | $1.1 \times 10^2$ | $8.9 \times 10$ |
| 44 | $1.0 \times 10^5$ | a | $4.1 \times 10$ | $5.6 \times 10$ | $5.5 \times 10$ | $8.5 \times 10$ | $7.8 \times 10$ |
|  |  | b | $4.3 \times 10$ | $5.8 \times 10$ | $5.6 \times 10$ | $8.5 \times 10$ | $7.8 \times 10$ |
| 66 | $1.5 \times 10^5$ | a | $2.7 \times 10$ | $6.4 \times 10$ | $5.3 \times 10$ | $3.7 \times 10$ | $6.1 \times 10$ |
|  |  | b | $2.7 \times 10$ | $6.5 \times 10$ | $5.3 \times 10$ | $3.7 \times 10$ | $6.1 \times 10$ |

*Culture duration a: 48 hours b: 96 hours (5—5). Result 4C-1
<1> Result of the inactivation test
<2> Fungi density: $10^3$ order/ml

TABLE 11

| UV Radiation Time (sec) | UV Radiation Quantity ($\mu W \cdot s/cm^2$) | Test 1 | Test 2 | Test 3 | Test 4 | Test 5 | Average (Sterilization rate %) |
|---|---|---|---|---|---|---|---|
| 0 | 0 | $1.9 \times 10^3$ | $1.7 \times 10^3$ | $2.1 \times 10^3$ | $1.9 \times 10^3$ | $1.9 \times 10^3$ | $1.9 \times 10^3$ |
| 22 | $5.0 \times 10^4$ | $5.2 \times 10^2$ | $4.4 \times 10^2$ | $5.6 \times 10^2$ | $5.2 \times 10^2$ | $7.2 \times 10^2$ | $5.5 \times 10^2$ (71.1) |
| 44 | $1.0 \times 10^5$ | $5.8 \times 10^2$ | $6.6 \times 10^2$ | $7.8 \times 10^2$ | $4.8 \times 10^2$ | $5.6 \times 10^2$ | $6.1 \times 10^2$ (67.9) |
| 66 | $1.5 \times 10^5$ | $5.2 \times 10^2$ | $4.2 \times 10^2$ | $4.0 \times 10^2$ | $6.0 \times 10^2$ | $7.8 \times 10^2$ | $5.4 \times 10^2$ (71.6) |

(5-6) Result 4C-2
<1> Result of the inactivation test [Culture duration and degree of colony outbreak]
<2> Fungi density: $10^3$ order/ml

TABLE 12

| UV Radiation Time (sec) | UV Radiation Quantity ($\mu W \cdot s/cm^2$) | * | Test 1 | Test 2 | Test 3 | Test 4 | Test 5 |
|---|---|---|---|---|---|---|---|
| 0 | 0 | a | $1.9 \times 10^3$ | $1.7 \times 10^3$ | $2.1 \times 10^3$ | $1.9 \times 10^3$ | $1.9 \times 10^3$ |
|   |   | b | $1.9 \times 10^3$ | $1.7 \times 10^3$ | $2.1 \times 10^3$ | $3.9 \times 10^3$ | $1.9 \times 10^3$ |
| 22 | $5.0 \times 10^4$ | a | $5.2 \times 10^2$ | $4.4 \times 10^2$ | $5.6 \times 10^2$ | $5.2 \times 10^2$ | $7.2 \times 10^2$ |
|   |   | b | $5.2 \times 10^2$ | $4.4 \times 10^2$ | $5.6 \times 10^2$ | $5.2 \times 10^2$ | $7.2 \times 10^2$ |
| 44 | $1.0 \times 10^5$ | a | $5.8 \times 10^2$ | $6.4 \times 10^2$ | $7.6 \times 10^2$ | $4.6 \times 10^2$ | $5.4 \times 10^2$ |
|   |   | b | $5.8 \times 10^2$ | $6.6 \times 10^2$ | $7.8 \times 10^2$ | $4.8 \times 10^2$ | $5.6 \times 10^2$ |
| 66 | $1.5 \times 10^5$ | a | $5.2 \times 10^2$ | $4.2 \times 10^2$ | $3.8 \times 10^2$ | $6.0 \times 10^2$ | $7.4 \times 10^2$ |
|   |   | b | $5.2 \times 10^2$ | $4.2 \times 10^2$ | $4.0 \times 10^2$ | $6.0 \times 10^2$ | $7.8 \times 10^2$ |

*Culture duration a: 48 hours b: 96 hours (6) Discussion

As shown in Tables 7, 9 and 11, UV tolerance of *Chaetomium globosum* lowered its initial order, but there was not influence and change on the sterilization effect any more, even if UV quantity was raised. Further, no marked proliferation of fungi once sterilized was observed in 96 hours, as shown in Tables 8, 10 and 12.

Experiment 5

(1) Title of Test

Inactivation test by UV sterilization lamp against *Chaetomium globosum*

(2) Object

UV tolerance of *Chaetomium globosum* was ensured by irradiating strong UV over the fungi, and fungi proliferation rate after culturing the mold for 48 hours and 96 hours, which had been sterilized by the strong UV radiation, was examined.

(3) Test Fungi and Quantity

*Chaetomium globosum* ATCC6205 1 strain (4) Test Condition

UV sterilization lamp: SGL-1000T5 HOSHIN 1

Distance from the lamp pipe wall: 300 mm

UV value at stable time: 2300 $\mu W/cm^2$

Test container/Fungi liquid quantity: 90 mm watch-glass shaped plate/1 ml n=3 (Result in Table: Number of fungi in 1 ml)

Test fungi density: $10^3$ to $10^4$/ml

UV radiation time (sec): 0, 22, 44, 65, 87, 109, 130

UV radiation quantity ($\mu W \cdot s/cm2$): Result was described in Table.

Adjustment of Test fungi: Fungi were spread on potato dextrose agar plating medium 1 week before the test initiation, and the fungi were cultured at 27±2° C. and provided for the test.

Counting number of fungi: Agar dilution method

Culture condition: potato dextrose agar medium, 27±2° C., 96 hours (5-1) Result 5-A Result of the inactivation test

TABLE 13

| UV Radiation Time (sec) | UV Radiation Quantity ($\mu W \cdot s/cm^2$) | Test 1 | Test 2 | Test 3 |
|---|---|---|---|---|
| 0 | 0 | $4.9 \times 10^3$ | $3.7 \times 10^3$ | $4.3 \times 10^3$ |
| 22 | $5.0 \times 10^4$ | $1.3 \times 10^2$ | $1.4 \times 10^2$ | $1.5 \times 10^2$ |
| 44 | $1.0 \times 10^5$ | $1.0 \times 10^2$ | $1.0 \times 10^2$ | $1.2 \times 10^2$ |
| 65 | $1.5 \times 10^5$ | $4.6 \times 10$ | $4.5 \times 10$ | $5.7 \times 10$ |
| 87 | $2.0 \times 10^5$ | $4.7 \times 10$ | $7.2 \times 10$ | $4.2 \times 10$ |
| 109 | $2.5 \times 10^5$ | $4.6 \times 10$ | $4.0 \times 10$ | $3.6 \times 10$ |
| 130 | $3.0 \times 10^5$ | $5.2 \times 10$ | $3.8 \times 10$ | $5.2 \times 10$ |

Culture duration 96 hours (5-2) Result 5-B

Result of the inactivation test [Culture duration and degree of colony outbreak]

TABLE 14

| UV Radiation Time (sec) | UV Radiation Quantity ($\mu W \cdot s/cm^2$) | Test 1 48 hours | Test 1 96 hours | Test 2 48 hours | Test 2 96 hours | Test 3 48 hours | Test 3 96 hours |
|---|---|---|---|---|---|---|---|
| 0 | 0 | $2.9 \times 10^3$ | $4.9 \times 10^3$ | $3.0 \times 10^3$ | $3.7 \times 10^3$ | $2.7 \times 10^3$ | $4.3 \times 10^3$ |
| 22 | $5.0 \times 10^4$ | $1.2 \times 10^2$ | $1.3 \times 10^2$ | $1.3 \times 10^2$ | $1.4 \times 10^2$ | $1.3 \times 10^2$ | $1.5 \times 10^2$ |
| 44 | $1.0 \times 10^5$ | $9.1 \times 10$ | $1.0 \times 10^2$ | $8.0 \times 10$ | $1.0 \times 10^2$ | $1.0 \times 10^2$ | $1.2 \times 10^2$ |
| 65 | $1.5 \times 10^5$ | $3.7 \times 10$ | $4.6 \times 10$ | $3.1 \times 10$ | $4.5 \times 10$ | $2.3 \times 10$ | $5.7 \times 10$ |
| 87 | $2.0 \times 10^5$ | $3.2 \times 10$ | $4.7 \times 10$ | $6.6 \times 10$ | $7.2 \times 10$ | $2.4 \times 10$ | $4.2 \times 10$ |
| 109 | $2.5 \times 10^5$ | $2.6 \times 10$ | $4.6 \times 10$ | $2.1 \times 10$ | $4.0 \times 10$ | $2.3 \times 10$ | $3.6 \times 10$ |
| 130 | $3.0 \times 10^5$ | $2.6 \times 10$ | $5.2 \times 10$ | $4.2 \times 10$ | $3.8 \times 10$ | $4.4 \times 10$ | $5.2 \times 10$ |

(6) Discussion

As shown in Table 13, no more effect than 90% by 50 mW, 99% by 200 mW and 99% by 300 mW was seen even by raising UV radiation. Further, there was hardly observed any difference between culturing for 48 hours and 96 hours.

Experiment 6

(1) Title of Test

Inactivation test by UV sterilization lamp against *Chaetomium globosum*

(2) Object

UV tolerance was ensured by irradiating very strong UV over *Chaetomium globosum*, and fungi proliferation rate after culturing the fungi for 48 hours and 96 hours, which had been sterilized by the strong UV radiation was examined.

(3) Test Fungi and Quantity *Chaetomium globosum* ATCC6205 1 strain (4) Test Condition UV sterilization lamp: SGL-1000T5 HOSHIN 1

Distance from the lamp pipe wall: 300 mm

UV value at stable time: 2300 $\mu W/cm^2$

Test container/Fungi liquid quantity: 90 mm watch-glass shaped plate/1 ml n=3 (Result in Table: Number of fungi in 1 ml)

Test fungi density: $10^3$ to $10^4$/ml

UV radiation time (sec): 0, 130, 174, 218, 261, 305, 348, 392, 435

UV radiation quantity ($\mu W \cdot s/cm^2$): Result was described in Table.

Adjustment of Test fungi: Fungi were spread on potato dextrose agar plating medium 1 week before the test initiation, and the fungi were cultured at 27±2° C. and provided for the test.

Counting number of fungi: Agar dilution method

Culture condition: potato dextrose agar medium, 27±2° C., 96 hours (5-1) Result 6-A Result of the inactivation test

TABLE 15

| UV Radiation Time (sec) | UV Radiation Quantity ($\mu W \cdot s/cm^2$) | Test 1 | Test 2 | Test 3 |
|---|---|---|---|---|
| 0 | 0 | $9.6 \times 10^3$ | $1.1 \times 10^4$ | $1.0 \times 10^4$ |
| 130 | $3.0 \times 10^5$ | $3.7 \times 10^2$ | $3.7 \times 10^2$ | $6.0 \times 10^2$ |
| 174 | $4.0 \times 10^5$ | $1.3 \times 10^2$ | $2.0 \times 10^2$ | $2.2 \times 10^2$ |
| 218 | $5.0 \times 10^5$ | $8.1 \times 10$ | $2.0 \times 10^2$ | $1.1 \times 10^2$ |
| 261 | $6.0 \times 10^5$ | $1.8 \times 10^2$ | $3.4 \times 10$ | $1.3 \times 10^2$ |
| 305 | $7.0 \times 10^5$ | $6.8 \times 10$ | $8.3 \times 10$ | $9.3 \times 10$ |
| 348 | $8.0 \times 10^5$ | $8.6 \times 10$ | $6.2 \times 10$ | $9.4 \times 10$ |
| 392 | $9.0 \times 10^5$ | $5.3 \times 10$ | $5.7 \times 10$ | $6.0 \times 10$ |
| 435 | $1.0 \times 10^6$ | $7.1 \times 10$ | $4.6 \times 10$ | $5.1 \times 10$ |

Culture duration 96 hours (5-2) Result 6-B

Result of the inactivation test [Culture duration and degree of colony outbreak]

TABLE 16

| UV Radiation Time (sec) | UV Radiation Quantity ($\mu W \cdot s/cm^2$) | Test 1 48 hours | Test 1 96 hours | Test 2 48 hours | Test 2 96 hours | Test 3 48 hours | Test 3 96 hours |
|---|---|---|---|---|---|---|---|
| 0 | 0 | $8.5 \times 10^3$ | $9.6 \times 10^3$ | $8.7 \times 10^3$ | $1.1 \times 10^4$ | $9.1 \times 10^3$ | $1.0 \times 10^4$ |
| 130 | $3.0 \times 10^4$ | $3.7 \times 10^2$ | $3.7 \times 10^2$ | $3.6 \times 10^2$ | $3.7 \times 10^2$ | $5.8 \times 10^2$ | $6.0 \times 10^2$ |
| 174 | $4.0 \times 10^5$ | $1.3 \times 10^2$ | $1.3 \times 10^2$ | $1.9 \times 10^2$ | $2.0 \times 10^2$ | $2.2 \times 10^2$ | $2.2 \times 10^2$ |
| 218 | $5.0 \times 10^5$ | $7.7 \times 10$ | $8.1 \times 10$ | $2.0 \times 10^2$ | $2.0 \times 10^2$ | $1.1 \times 10^2$ | $1.1 \times 10^2$ |
| 261 | $6.0 \times 10^5$ | $1.7 \times 10^2$ | $1.8 \times 10^2$ | $3.1 \times 10$ | $3.4 \times 10$ | $1.2 \times 10^2$ | $1.3 \times 10^2$ |
| 305 | $7.0 \times 10^5$ | $6.6 \times 10$ | $6.8 \times 10$ | $8.1 \times 10$ | $8.3 \times 10$ | $8.8 \times 10$ | $9.3 \times 10$ |
| 348 | $8.0 \times 10^5$ | $7.9 \times 10$ | $8.6 \times 10$ | $5.7 \times 10$ | $6.2 \times 10$ | $9.1 \times 10$ | $9.4 \times 10$ |
| 392 | $9.0 \times 10^5$ | $4.9 \times 10$ | $5.3 \times 10$ | $5.4 \times 10$ | $5.7 \times 10$ | $5.7 \times 10$ | $6.0 \times 10$ |
| 435 | $1.0 \times 10^6$ | $6.4 \times 10$ | $7.1 \times 10$ | $4.1 \times 10$ | $4.6 \times 10$ | $4.7 \times 10$ | $5.1 \times 10$ |

(6) Discussion

As shown in Table 15, sterilization rate was not raised even by irradiating strong UV rays in case of fungi number below 100 order, showing almost the same result as in higher UV radiation. Further, there was hardly observed any difference between culturing for 48 hours and 96 hours.

Experiment 7

(1) Title of Test
Inactivation test by UV sterilization lamp against *Chaetomium globosum*
(2) Object
Thermal tolerance against *Chaetomium globosum* was ensured, and by performing further UV radiation as it was, fungi proliferation rate after culturing the fungi for 48 hours and 96 hours, which had been sterilized was examined.
(3) Test Fungi and Quantity
*Chaetomium globosum* ATCC6205 1 strain
(4) Test Condition
UV sterilization lamp: SGL-1000T5 HOSHIN 1
Distance from the lamp pipe wall: 300 mm
UV value at stable time: 2300 $\mu W/cm^2$
Test container/Fungi liquid quantity: 90 mm watch-glass shaped plate/1 ml n=2 (Result in Table: Number of fungi in 1 ml)
Test fungi density: $10^3$ to $10^4$/ml
UV radiation time (sec): 0, 22, 44, 66
UV radiation quantity ($\mu W \cdot s/cm2$): Result was described in Table.
Adjustment of Test fungi: Fungi were spread on potato dextrose agar plating medium 1 week before the test initiation. The fungi were cultured at 27±2° C., kept at 35° C., 40° C., 45° C., 50° C. and 60° C. each for about 5 minutes and subjected to UV radiation as it was.
Counting number of fungi: Agar dilution method
Culture condition: potato dextrose agar medium, 27±2° C., 96 hours
(5-1) Result 7-A
<1> Result of the Inactivation test [culture duration and degree of colony outbreak]
<2> Fungi heated at 35° C., 40° C., 45° C., 50° C., and 60° C. each for about 5 minutes

TABLE 17

| UV Radiation Time (sec) | UV Radiation Quantity ($\mu W \cdot s/cm^2$) | n | 35° C. | 40° C. | 45° C. | 50° C. | 60° C. |
| --- | --- | --- | --- | --- | --- | --- | --- |
| 0 | 0 | 1 | $2.6 \times 10^3$ | $2.2 \times 10^3$ | $2.1 \times 10^3$ | $1.4 \times 10^3$ | 2 |
|  |  | 2 | $3.0 \times 10^3$ | $2.8 \times 10^3$ | $2.8 \times 10^3$ | $1.4 \times 10^3$ | 3 |
| 22 | $5.0 \times 10^4$ | 1 | $2.2 \times 10^2$ | $2.3 \times 10^2$ | $2.1 \times 10^2$ | $2.7 \times 10^2$ | 1 |
|  |  | 2 | $2.3 \times 10^2$ | $1.9 \times 10^2$ | $2.1 \times 10^2$ | $1.5 \times 10^2$ | 1 |
| 44 | $1.0 \times 10^5$ | 1 | $2.5 \times 10^2$ | $2.2 \times 10^2$ | $2.2 \times 10^2$ | $1.4 \times 10^2$ | 0 |
|  |  | 2 | $1.8 \times 10^2$ | $1.7 \times 10^2$ | $1.6 \times 10^2$ | $1.3 \times 10^2$ | 1 |
| 66 | $1.5 \times 10^5$ | 1 | $1.5 \times 10^2$ | $2.4 \times 10^2$ | $2.4 \times 10^2$ | $1.9 \times 10^2$ | 0 |
|  |  | 2 | $1.9 \times 10^2$ | $1.1 \times 10^2$ | $1.3 \times 10^2$ | $1.4 \times 10^2$ | 0 |

(5-2) Result 7A-1
Thermal treatment at 35° C. for 5 minutes

TABLE 18

| UV Radiation Time (sec) | UV Radiation Quantity ($\mu W \cdot s/cm^2$) | Test 1 | | Test 2 | |
| --- | --- | --- | --- | --- | --- |
|  |  | 48 hours | 96 hours | 48 hours | 96 hours |
| 0 | 0 | $2.5 \times 10^3$ | $2.6 \times 10^3$ | $2.9 \times 10^3$ | $3.0 \times 10^3$ |
| 22 | $5.0 \times 10^4$ | $2.1 \times 10^2$ | $2.2 \times 10^2$ | $2.3 \times 10^2$ | $2.3 \times 10^2$ |
| 44 | $1.0 \times 10^5$ | $2.5 \times 10^2$ | $2.5 \times 10^2$ | $1.7 \times 10^2$ | $1.8 \times 10^2$ |
| 66 | $1.5 \times 10^5$ | $1.5 \times 10^2$ | $1.5 \times 10^2$ | $1.9 \times 10^2$ | $1.9 \times 10^2$ |

(5-3) Result 7A-2

Thermal treatment at 40° C. for 5 minutes

TABLE 19

| UV Radiation Time (sec) | UV Radiation Quantity ($\mu W \cdot s/cm^2$) | Test 1 | | Test 2 | |
| --- | --- | --- | --- | --- | --- |
|  |  | 48 hours | 96 hours | 48 hours | 96 hours |
| 0 | 0 | $2.2 \times 10^3$ | $2.2 \times 10^3$ | $2.8 \times 10^3$ | $2.8 \times 10^3$ |
| 22 | $5.0 \times 10^4$ | $2.3 \times 10^2$ | $2.3 \times 10^2$ | $1.8 \times 10^2$ | $1.9 \times 10^2$ |
| 44 | $1.0 \times 10^5$ | $2.1 \times 10^2$ | $2.2 \times 10^2$ | $1.7 \times 10^2$ | $1.7 \times 10^2$ |
| 66 | $1.5 \times 10^5$ | $2.3 \times 10^2$ | $2.4 \times 10^2$ | $1.1 \times 10^2$ | $1.1 \times 10^2$ |

(5-4) Result 7A-3

Thermal treatment at 45° C. for 5 minutes

TABLE 20

| UV Radiation Time (sec) | UV Radiation Quantity ($\mu W \cdot s/cm^2$) | Test 1 | | Test 2 | |
| --- | --- | --- | --- | --- | --- |
|  |  | 48 hours | 96 hours | 48 hours | 96 hours |
| 0 | 0 | $2.1 \times 10^3$ | $2.1 \times 10^3$ | $2.7 \times 10^3$ | $2.8 \times 10^3$ |
| 22 | $5.0 \times 10^4$ | $2.1 \times 10^2$ | $2.0 \times 10^2$ | $2.0 \times 10^2$ | $2.1 \times 10^2$ |
| 44 | $1.0 \times 10^5$ | $2.1 \times 10^2$ | $1.6 \times 10^2$ | $2.2 \times 10^2$ | $1.6 \times 10^2$ |
| 66 | $1.5 \times 10^5$ | $2.4 \times 10^2$ | $1.3 \times 10^2$ | $2.4 \times 10^2$ | $1.3 \times 10^2$ |

(5—5) Result 7A-4
Thermal treatment at 50° C. for 5 minutes

TABLE 21

| UV Radiation Time (sec) | UV Radiation Quantity ($\mu W \cdot s/cm^2$) | Test 1 | | Test 2 | |
| --- | --- | --- | --- | --- | --- |
|  |  | 48 hours | 96 hours | 48 hours | 96 hours |
| 0 | 0 | $1.4 \times 10^3$ | $1.4 \times 10^3$ | $1.4 \times 10^3$ | $1.4 \times 10^3$ |
| 22 | $5.0 \times 10^4$ | $2.6 \times 10^2$ | $2.7 \times 10^2$ | $1.5 \times 10^2$ | $1.5 \times 10^2$ |
| 44 | $1.0 \times 10^5$ | $1.4 \times 10^2$ | $1.4 \times 10^2$ | $1.3 \times 10^2$ | $1.3 \times 10^2$ |
| 66 | $1.5 \times 10^5$ | $1.9 \times 10^2$ | $1.9 \times 10^2$ | $1.4 \times 10^2$ | $1.4 \times 10^2$ |

(5-6) Result 7A-5
Thermal treatment at 60° C. for 5 minutes

TABLE 22

| UV Radiation Time (sec) | UV Radiation Quantity ($\mu W \cdot s/cm^2$) | Test 1 | | Test 2 | |
|---|---|---|---|---|---|
| | | 48 hours | 96 hours | 48 hours | 96 hours |
| 0 | 0 | 2 | 3 | 2 | 3 |
| 22 | $5.0 \times 10^4$ | 1 | 1 | 1 | 1 |
| 44 | $1.0 \times 10^5$ | 0 | 1 | 0 | 1 |
| 66 | $1.5 \times 10^5$ | 0 | 0 | 0 | 0 |

(6) Discussion

As shown in Tables 17 to 21, there was almost no sterilization effect up to 50° C. on thermal tolerance of *Chaetomium globosum*. As shown in Tables 17 and 22, the effect was 99.9% at 60° C. Then, 50 mW/100 mW UV radiation was effective. Survived number near zero can be achieved by UV radiation of about 150 mW.

Experiment 8

(1) Title of Test

Inactivation test (thermal post-treatment) by UV sterilization lamp against *Chaetomium globosum*

(2) Object

Thermal tolerance and UV radiation test against *Chaetomium globosum* were ensured in the former stage, and in this case, UV radiation, followed by heating, was examined on the contrary, while observing the difference between this case and the former stage. Further, whether there is any growth of fungi once sterilized or remaining at that time by culturing for 48 and 96 hours respectively was also examined.

(3) Test Fungi and Quantity

*Chaetomium globosum* ATCC6205 1 strain (4) Test Condition

UV sterilization lamp: SGL-1000T5 HOSHIN 1

Distance from the lamp pipe wall: 300 mm

UV value at stable time: 2300 $\mu W/cm^2$

Test container/Fungi liquid quantity: 90 mm watch-glass shaped plate/1 ml n=2

(Result in Table: Number of fungi in 1 m 1)

Test fungi density: $10^3$ to $10^4$/ml

UV radiation time (sec): 0, 22, 44, 66

UV radiation quantity ($\mu W \cdot s/cm^2$): Result was described in Table.

Adjustment of Test fungi: Fungi were spread on a potato dextrose agar plating medium 1 week before the test initiation, and the fungi were cultured at 27±2° C., subjected to UV radiation and heated at 45° C., 50° C. and 60° C. each for 5 minutes.

Counting number of fungi: Agar dilution method

Culture condition: potato dextrose agar medium, 27±2° C., 96 hours (5-1) Result 8-A <1> Result of the inactivation test [culture duration and degree of colony outbreak]

<2> After UV radiation, thermal treatment at 45° C., 50° C. and 60° C. each was done for 5 minutes.

TABLE 23

| UV Radiation Time (sec) | UV Radiation Quantity ($\mu W \cdot s/cm^2$) | n | Thermal treating time 45° C. | Thermal treating time 50° C. | Thermal treating time 60° C. |
|---|---|---|---|---|---|
| 0 | 0 | 1 | $5.0 \times 10^2$ | $3.0 \times 10^2$ | 3 |
| | | 2 | $8.0 \times 10^2$ | $4.0 \times 10^2$ | 0 |
| 22 | $5.0 \times 10^4$ | 1 | $2.1 \times 10^2$ | $2.3 \times 10^2$ | 0 |
| | | 2 | $2.0 \times 10^2$ | $7.9 \times 10$ | 0 |
| 44 | $1.0 \times 10^5$ | 1 | $1.5 \times 10^2$ | $1.5 \times 10^2$ | 0 |
| | | 2 | $8.7 \times 10$ | $9.5 \times 10$ | 0 |
| 66 | $1.5 \times 10^5$ | 1 | $1.2 \times 10^2$ | $7.8 \times 10$ | 0 |
| | | 2 | $8.8 \times 10$ | $8.4 \times 10$ | 0 |

(5-2) Result 8A-1
Thermal treatment at 45° C. for about 5 minutes

TABLE 24

| UV Radiation Time (sec) | UV Radiation Quantity ($\mu W \cdot s/cm^2$) | Test 1 | | Test 2 | |
|---|---|---|---|---|---|
| | | 48 hours | 96 hours | 48 hours | 96 hours |
| 0 | 0 | $5.0 \times 10^2$ | $5.0 \times 10^2$ | $8.0 \times 10^2$ | $8.0 \times 10^2$ |
| 22 | $5.0 \times 10^4$ | $2.1 \times 10^2$ | $2.1 \times 10^2$ | $2.0 \times 10^2$ | $2.0 \times 10^2$ |
| 44 | $1.0 \times 10^5$ | $1.5 \times 10^2$ | $1.5 \times 10^2$ | $7.9 \times 10$ | $8.7 \times 10$ |
| 66 | $1.5 \times 10^5$ | $1.2 \times 10^2$ | $1.2 \times 10^2$ | $8.3 \times 10$ | $8.8 \times 10$ |

(5-3) Result 8A-2
Thermal treatment at 50° C. for about 5 minutes

TABLE 25

| UV Radiation Time (sec) | UV Radiation Quantity ($\mu W \cdot s/cm^2$) | Test 1 | | Test 2 | |
|---|---|---|---|---|---|
| | | 48 hours | 96 hours | 48 hours | 96 hours |
| 0 | 0 | $3.0 \times 10^2$ | $3.0 \times 10^2$ | $2.0 \times 10^2$ | $4.0 \times 10^2$ |
| 22 | $5.0 \times 10^4$ | $2.2 \times 10^2$ | $2.3 \times 10^2$ | $7.4 \times 10$ | $7.9 \times 10$ |
| 44 | $1.0 \times 10^5$ | $8.9 \times 10$ | $9.5 \times 10$ | $1.4 \times 10^2$ | $1.5 \times 10^2$ |
| 66 | $1.5 \times 10^5$ | $7.1 \times 10$ | $7.8 \times 10$ | $7.5 \times 10$ | $8.4 \times 10$ |

(5-4) Result 8A-3
Thermal treatment at 60° C. for about 5 minutes

TABLE 26

| UV Radiation Time (sec) | UV Radiation Quantity ($\mu W \cdot s/cm^2$) | Test 1 | | Test 2 | |
|---|---|---|---|---|---|
| | | 48 hours | 96 hours | 48 hours | 96 hours |
| 0 | 0 | 3 | 3 | 3 | 3 |
| 22 | $5.0 \times 10^4$ | 0 | 0 | 0 | 0 |
| 44 | $1.0 \times 10^5$ | 0 | 0 | 0 | 0 |
| 66 | $1.5 \times 10^5$ | 0 | 0 | 0 | 0 |

(6) Discussion

As shown in Table 23 and 24, an effect of 59% was attained by 100 mW of UV radiation before the thermal treatment at around 45° C., and there was not seen any considerable change by the thermal treatment at 50° C., even if 100 mW of UV was irradiated prior to heating, as shown in Tables 23 and 25. However, it was confirmed that the remaining *Chaetomium globosum* was close to zero by holding it at 60° C. for 5 minutes after the radiation of 50 mW UV, as shown in Tables 23 and 26. Thus, it was confirmed that *Chaetomium globosum* was killed by irradiating 50 mW/100 mW UV and heating it at 60° C. for 5 minutes.

Accordingly, practical embodiments of the present invention have been explained, but the scope of the invention should not be limited to them. For example, sterilization is performed by irradiating UV with UV Radiation Device 3 from about Device 1 and pouring heated water by Heated Water Supplying Device 4 in the embodiments. However, the sterilization may be also performed by treating it from other directions such as sideward, downwards, inside, etc. or sterilizing the whole Container 1. Further, as means for heating Container 1, heated water is used herein. However, not only medium heating means using hot wind or another heated medium may be, of course, applied but also electromagnetic wave heating means irradiating infrared light, far infrared light, laser beam, or other electromagnetic wave may be adopted. In this case, it is preferable to irradiate not less than $5.0 \times 10^4$ $\mu W \cdot s/cm^2$ of UV in wave length of 180 nm to 480 nm. Further, heat may be applied by irradiating UV rays over the air, which would be the source of hot wind.

Moreover, when a longer time for heating is needed because the temperature for applying heat against Container 1 is as low as 55° C. to 85° C., it may be preferable to take means of establishing a passageway of spiral structure and so on in order to find time to heat. On the other hand, it may be, of course, possible to shorten the time needed for applying heated medium or the time needed for irradiating the electromagnetic wave if the temperature of heated medium is 85° C. to 99° C., a sterilization target such as fungi etc. itself is heated at 85° C. to 99° C. or further higher temperature is applied.

In particular, in case of heating a sterilization target, a time of 5 to 6 minutes is necessary for applying heating medium or irradiating electromagnetic beam if the temperature of the heated medium or the sterilization target is brought at 55° C. to 85° C. within one minute soon after irradiating UV rays. When heated medium or a sterilization target is brought to temperature of 85° C. to 99° C. on the contrary, shorter time is needed to accomplish the objective, such as 2 to 30 seconds for applying heated medium or irradiating electromagnetic beam.

In this way, the present invention can take various ways within the scope that does not deviate from the purpose of the invention.

Industrial Applicability

According to a method of sterilizing fungi and/or bacteria in a spore state in the present invention, by irradiating ultraviolet rays to the portions to be sterilized of target-adhering things such as containers, packing materials, conveying tools, etc. and target-containing things such as liquid, air, raw materials, etc. to hurt the fungi and so on adhering onto the target-adhering things and the fungi and so on contained in the target-containing things, followed by heating the fungi and so by applying heated medium such as heated water, hot wind, etc. over the fungi and so on, or by heating the portions to be sterilized in the target-containing things to give thermal stimulation to the fungi and so on adhering onto the target-adhering things and the fungi and so on contained in the target-containing things followed by irradiating ultraviolet rays over the fungi and so on, fungi and bacteria in a spore state can be sterilized effectively by collaboration of UV rays and heat to prevent contamination of the target-adhering things, target-containing things and circumstances thereof.

Further, according to a sterilizer against fungi and/or bacteria in a spore state in the present invention, there can be provided a device enabling to effectively, simply and certainly sterilize the fungi and so on/or bacteria in a spore state which are strong against UV rays but fragile against heat and the fungi and so on which are strong against heat but fragile against UV rays by collaboration of UV rays and heat. The sterilizer comprises UV radiation means and heating means for irradiating ultraviolet rays over the sterilization target to hurt it and heating the sterilization target, or for heating the sterilization target to give thermal stimulation to the sterilization target and irradiating UV rays over the sterilization target.

Description of Reference Numerals

1 . . . CONTAINER
2 . . . UV IRRADIATION ZONE
3 . . . HEAT TREATMENT ZONE
4 . . . HEATING DEVICE
10 . . . GERM-FREE FILLING DEVICE
11 . . . PRELIMINARY WASHING DEVICE
15 . . . FILLING DEVICE
18, 19, 20, 21 . . . STERILIZER

What is claimed is:

1. A method of sterilizing fungi and/or bacteria in a spore states which comprises irradiating ultraviolet rays at a dosage of at least $5.0 \times 10^4$ $\mu W \cdot s/cm^2$ over portions to be sterilized on target-adhering things and on target-containing things to hurt said spores adhering to the target-adhering things or contained in the target containing things, and then heating said snores to kill them, wherein said target-adhering things comprise containers, packing materials and conveying tools, and said target-containing things comprise liquid, air and raw materials.

2. A method of sterilizing fungi and/or bacteria in a spore state, which comprises heating portions to be sterilized on target-adhering things and on target-containing things to give thermal stimulation to said spores adhering to the target-adherent things or contained in the target-container things, and then irradiating said spores with ultraviolet rays at a dosage of at least $5.0 \times 10^4$ $\mu W \cdot s/cm^2$ to kill said spores, wherein said target-adhering things comprise containers, packing materials and conveying tools, and said target-containing things comprise liquid, air and raw materials.

3. The method of sterilizing fungi and/or bacteria in a spore state according to claim 1, wherein said irradiation is performed by irradiating not less than $5.0 \times 10^4$ $\mu W \cdot s/cm^2$ of ultraviolet rays at a wave length of from 180 nm to 480 nm.

4. The method of sterilizing fungi and/or bacteria in a spore state according to claim 1, wherein said spores are heated by applying a heated medium at 55° C. to 100° C.

5. The method of sterilizing fungi and/or bacteria in a spore state according to claim 1, wherein said spores are heated at 55° C. to 100° C. by electromagnetic wave radiation.

6. A system for sterilizing fungi and/or bacteria in a spore state1 comprising:
   a UV radiation element adapted to irradiate at a dosage of at least $5.0 \times 10^4$ $\mu W \cdot s/cm^2$ portions to be sterilized on target-adhering things or on target-containing things to hurt sterilization targets adhering to the target-adhering things or contained in the target containing things, and
   a heating element for heating said spores hurt by the UV radiation,
wherein said target-adhering things comprise containers, packing materials and conveying tools, and said target-containing things comprise liquid, air and raw materials.

7. A system for sterilizing fungi and/or bacteria in a spore state comprising:
- a heating element for heating portions to be sterilized on target-adhering things or on target-containing things to give thermal stimulation to said spores adhering to the target-adherent things or contained in the target-container things; and
- a UV radiation element for irradiating ultraviolet rays at a dosage of at least $5.0 \times 10^4$ $\mu$W·s/cm$^2$ over said spores having received the thermal stimulation, wherein said target-adhering things comprise containers, packing materials and conveying tools, and said target-containing things comprise liquid, air and raw materials.

8. The system according to claim 6, wherein said heating element comprises water, wind and steam.

9. The system according to claim 6, wherein said heating element comprises electromagnetic radiation and a laser beam.

10. The system according to claim 6, wherein said UV radiation element irradiates said spores at a wave length ranging from 108 nm to 480 nm.

11. The method of sterilizing fungi and/or bacteria in a spore state according to claim 2, wherein said spores are irradiated at a wave length of from 180 nm to 480 nm.

12. The method of sterilizing fungi and/or bacteria in a spore state according to claim 2, wherein said spores are heated at 55° C. to 100° C.

13. The method of sterilizing fungi and/or bacteria in a spore state according to claim 2, wherein said spores are heated by electromagnetic wave radiation.

14. The system according to claim 7, wherein said heating element comprises water, wind and steam.

15. The system according to claim 7, wherein said heating element comprises electromagnetic radiation and a laser beam.

16. The system according to claim 7, wherein said UV radiation element irradiates said spores at a wave length ranging from 108 nm to 480 nm.

* * * * *